(12) United States Patent
Keil (10) Patent No.: US 9,066,689 B2
(45) Date of Patent: Jun. 30, 2015

(54) LANCET WHEEL AND METHOD FOR PRODUCING A LANCET WHEEL

(75) Inventor: Michael Keil, Ludwigshafen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1276 days.

(21) Appl. No.: 12/891,844

(22) Filed: Sep. 28, 2010

(65) Prior Publication Data

US 2011/0015661 A1    Jan. 20, 2011

Related U.S. Application Data

(63) Continuation of application No. PCT/EP2009/003057, filed on Apr. 28, 2009.

(30) Foreign Application Priority Data

May 3, 2008    (EP) .................................... 08008393

(51) Int. Cl.
*A61B 17/32* (2006.01)
*A61B 5/15* (2006.01)
*A61B 5/151* (2006.01)

(52) U.S. Cl.
CPC ......... *A61B 5/1411* (2013.01); *Y10T 29/49986* (2015.01); *A61B 5/15146* (2013.01)

(58) Field of Classification Search
CPC ............... A61B 5/1405; A61B 5/1411; A61B 5/14532; A61B 5/15142; A61B 5/15144; A61B 5/15146; A61B 5/15148; A61B 5/15151; A61B 5/15153; A61B 5/15155; A61B 5/15157; A61B 5/15159; A61B 5/15161; A61B 5/15163; A61B 5/15174; A61B 5/150022

USPC .......................... 606/181–183; 600/573, 583
See application file for complete search history.

(56) References Cited

U.S. PATENT DOCUMENTS

| 4,794,926 | A | 1/1989 | Munsch et al. |
| 4,794,929 | A | 1/1989 | Maerfeld |
| 4,823,806 | A | 4/1989 | Bajada |

(Continued)

FOREIGN PATENT DOCUMENTS

| CN | 1456887 A | 11/2003 |
| EP | 0 985 376 A1 | 3/2000 |

(Continued)

OTHER PUBLICATIONS

International Application PCT/EP2009/003057 International Search Report and Written Opinion mailed Aug. 19, 2009 (German).

(Continued)

*Primary Examiner* — David Eastwood
(74) *Attorney, Agent, or Firm* — Woodard, Emhardt, Moriarty, McNett & Henry LLP (57) ABSTRACT

The invention relates to a lancet wheel comprising multiple annularly positioned lancets (3), which have a lancet body (3b) that is made of metal and ends in a lancet tip (3a), and a carrier (5), to which the lancets (3) are connected via radially running webs (6), which allow raising of the lancets (3) into the usage position. According to the invention, it is provided that the lancets (3) are radially aligned, and the webs (6) have a plastic body, which predefine an intended bending point, around which the webs (6) are bent to raise the lancets (3). Furthermore, the invention relates to a method for producing a lancet wheel.

16 Claims, 4 Drawing Sheets

(56) References Cited

U.S. PATENT DOCUMENTS

| | | |
|---|---|---|
| 5,395,388 A | 3/1995 | Schraga |
| 5,578,014 A | 11/1996 | Erez et al. |
| 5,647,851 A | 7/1997 | Pokras |
| 5,829,589 A | 11/1998 | Nguyen et al. |
| 5,921,963 A | 7/1999 | Erez et al. |
| 6,045,567 A | 4/2000 | Taylor et al. |
| 6,210,420 B1 | 4/2001 | Mauze et al. |
| 6,228,100 B1 | 5/2001 | Schraga |
| 6,231,531 B1 | 5/2001 | Lum et al. |
| 6,306,152 B1 | 10/2001 | Verdonk et al. |
| 7,004,928 B2 | 2/2006 | Aceti et al. |
| 7,150,755 B2 | 12/2006 | Levaughn et al. |
| 7,343,188 B2 | 3/2008 | Sohrab |
| 2001/0027328 A1 | 10/2001 | Lum et al. |
| 2002/0052618 A1 | 5/2002 | Haar et al. |
| 2002/0120216 A1 | 8/2002 | Fritz et al. |
| 2002/0130042 A1 | 9/2002 | Moerman et al. |
| 2002/0188224 A1 | 12/2002 | Roe et al. |
| 2003/0083686 A1 | 5/2003 | Freeman et al. |
| 2003/0191415 A1 | 10/2003 | Moerman et al. |
| 2003/0199895 A1 | 10/2003 | Boecker et al. |
| 2003/0199902 A1 | 10/2003 | Boecker et al. |
| 2003/0212347 A1 | 11/2003 | Sohrab |
| 2004/0039303 A1 | 2/2004 | Wurster et al. |
| 2004/0102803 A1 | 5/2004 | Boecker et al. |
| 2004/0193202 A1 | 9/2004 | Allen |
| 2005/0027211 A1 | 2/2005 | Kuhr et al. |
| 2005/0245845 A1 | 11/2005 | Roe et al. |
| 2006/0064035 A1 | 3/2006 | Wang et al. |
| 2006/0094985 A1 | 5/2006 | Aceti et al. |
| 2006/0178600 A1 | 8/2006 | Kennedy et al. |
| 2006/0200044 A1 | 9/2006 | Freeman et al. |
| 2006/0204399 A1 | 9/2006 | Freeman et al. |
| 2007/0142748 A1 | 6/2007 | Deshmukh et al. |
| 2007/0173741 A1 | 7/2007 | Deshmukh et al. |
| 2007/0179404 A1* | 8/2007 | Escutia et al. ............ 600/583 |
| 2007/0202338 A1 | 8/2007 | Sullivan |
| 2007/0292314 A1 | 12/2007 | Effenhauser et al. |
| 2008/0009768 A1 | 1/2008 | Sohrab |
| 2008/0021346 A1 | 1/2008 | Haar et al. |
| 2008/0269791 A1 | 10/2008 | Hoenes et al. |
| 2009/0099477 A1 | 4/2009 | Hoenes et al. |
| 2010/0174211 A1 | 7/2010 | Frey et al. |
| 2010/0234869 A1* | 9/2010 | Sacherer ............ 606/182 |

FOREIGN PATENT DOCUMENTS

| | | |
|---|---|---|
| EP | 1 074 219 A2 | 2/2001 |
| EP | 1 203 563 A2 | 5/2002 |
| EP | 1 360 934 A1 | 11/2003 |
| EP | 1 360 935 A1 | 11/2003 |
| EP | 1 402 812 A1 | 3/2004 |
| EP | 1 508 304 A1 | 2/2005 |
| EP | 1 658 897 A1 | 5/2006 |
| EP | 1 880 671 A1 | 1/2008 |
| EP | 2 050 392 A1 | 4/2009 |
| WO | WO 97/46157 A1 | 12/1997 |
| WO | WO 01/62150 A1 | 8/2001 |
| WO | WO 03/070099 A1 | 8/2003 |
| WO | WO 2005/006939 A2 | 1/2005 |
| WO | WO 2005/016125 A2 | 2/2005 |
| WO | WO 2005/033659 A2 | 4/2005 |
| WO | WO 2005/065415 A2 | 7/2005 |
| WO | WO 2005/118690 A1 | 12/2005 |
| WO | WO 2005/121759 A2 | 12/2005 |
| WO | WO 2006/038044 A2 | 4/2006 |
| WO | WO 2007/060004 A1 | 5/2007 |
| WO | WO 2007/084367 A2 | 7/2007 |

OTHER PUBLICATIONS

International Application PCT/EP2009/003057 International Search Report mailed Aug. 19, 2009 (translation).

Copending International Application PCT/EP2009/003057 International Preliminary Report on Patentability mailed Nov. 17, 2010.

* cited by examiner

LANCET WHEEL AND METHOD FOR PRODUCING A LANCET WHEEL

CROSS-REFERENCE TO RELATED APPLICATIONS

This application is a continuation of International Application No. PCT/EP2009/003057, filed Apr. 28, 2009, which claims the benefit of European Application No. 08008393.4, filed May 3, 2008. The entire disclosure of International Application No. PCT/EP2009/003057, filed Apr. 28, 2009, is hereby incorporated by reference.

BACKGROUND

The invention is directed to a lancet wheel having the features specified in the preamble of claim 1, as is known from EP 1 360 934 A1. Lancet wheels of this type are required, for example, for lancing systems, which are used by diabetics to obtain bodily fluid samples for determining the glucose content.

The lancets of the lancet wheel known from EP 1 360 934 A1 are connected to a carrier via webs fastened on both sides to the lancet body and are oriented in the peripheral direction. To raise the lancets into their usage position, the webs are twisted. Before the raising, the lancets are in the plane of the lancet wheel, so that the lancet tips are protected and the lancet wheel may be handled well in particular upon insertion into a lancing device.

This is an important advantage over the lancet wheels known from WO 2005/118690, in which lancets are moved within the plane of the lancet wheel for use by a toggle lever, so that the danger exists that injury will occur on a lancet tip during handling of such a lancet wheel.

The lancet wheel known from EP 1 360 934 A1 contains lancets in which an electrochemical sensor for measuring an analyte concentration is integrated. The lancets have a lancet body made of a substrate, on which a metal film is applied to form an electrode surface. The lancet body carries a reaction zone having detection chemicals, which is covered by a further substrate plate, which is also metal plated to form the second electrode surface. These lancets are embedded in plastic bodies, which are each connected via two metal webs to plastic rings of the lancet wheel.

However, a lancing system having the lancet wheels known from EP 1 360 934 A1 has the disadvantage of relatively high costs.

SUMMARY

The object of the invention is to show a way in which a lancing system having lancet wheels according to the preamble of claim 1 can be implemented more cost-effectively.

This object is achieved according to the invention by a lancet wheel having the features specified in claim 1. Advantageous refinements of the invention are the subject matter of the subclaims. The object is also achieved by a method for producing such a lancet wheel having the features specified in claim 11.

Because of the radial alignment of the lancets using radially running webs, a lancet wheel according to the invention can have an advantageously large number of lancets, which contributes to lowering the costs of the lancing system, because the costs per lancet may be reduced. In addition, only a single web is required for each lancet, which simplifies the production of the lancet wheel and also allows cost savings because of a simpler geometry.

Although a lancet wheel according to the invention can have substantially more lancets than is possible in the case of a lancet wheel known from EP 1 360 934 A1, the advantages of a flat configuration in a starting position, from which the lancets are raised for a puncture in a usage position, can be maintained, in that the webs, via which the lancets are connected to a carrier of the lancet wheel, are not twisted to align the lancets, but rather bent, preferably buckled, and have an intended bending point for this purpose.

The intended bending point can particularly advantageously be implemented in that the webs of a lancet wheel according to the invention are provided with a plastic body, which has a joint and predefines the intended bending point in this manner. For example, the plastic body can have a weakened point, for example, in the form of a notch or perforation, as the intended bending point, around which the webs are bent to raise the lancets.

The webs of a lancet wheel according to the invention are preferably bendable elastically around the intended bending point, so that an aligned lancet passes back into a flat location from the usage position after a puncture without external force action. This flat location is preferably the starting position of the lancet. However, it is also possible that a lancet snaps from the usage position into a flat location, in which it is oriented in reverse to the starting position. Because of the elastic mobility of the webs, a lancet in a lancing device can be brought into the usage position using a pivot unit, such as a pin which presses the lancet out of the wheel plane, and returns into a flat position itself as soon as the pivot unit no longer acts thereon. The plastic bodies of the webs according to the invention advantageously allow elastic properties which allow a bend around a right angle to raise the lancets and ensure a movement of the lancets into a flat location without external force action after a puncture.

A lancet wheel according to the invention can be produced cost-effectively in that a lancet wheel blank, which has annularly positioned lancets having a lancet body ending in a tip, are cut out of sheet metal and subsequently overmolded using plastic. The cutting out of the lancet wheel blank can be performed, for example, by laser cutting or punching, particularly advantageously by etching.

By the coating with plastic, plastic bodies which form the webs connecting the lancets to a carrier may be implemented cost-effectively and intended bending points for aligning the lancets may be predefined. A plastic body of a carrier connected to the webs can also be implemented. The plastic body of the carrier can merge into the plastic bodies of the lancets, so that the plastic bodies of the webs and the plastic bodies of the carrier are implemented integrally or in one piece.

A production method according to the invention advantageously manages using few handling and work steps. A one-piece lancet wheel blank may be cut out of sheet metal easily and subsequently laid in an injection mold. For a lancet wheel according to the invention, two parts are already sufficient per se, namely the lancet wheel blank and a plastic body injected around the lancet wheel blank, which can have webs having a predefined intended bending point. In addition, the lancet tips may advantageously be provided with a sterile protector with little effort, for example, in that the lancet tips are coated with injection molded foam.

The metal webs of the lancet wheel blank may be cut through and/or removed after it is placed in an injection mold, so that upon raising of the lancets, metal parts do not have to be bent. The work step connected to cutting through the metal webs may also be saved, however, in that the metal webs originating from the lancet bodies are embedded in the plastic bodies of the webs and extend through the intended bending point. The plastic body is preferably wider at the intended bending point than the metal web, it is particularly preferably at least twice as wide, in particular at least three times as wide. In this manner, the force application required for aligning a lancet is only insignificantly increased by the metal web.

An advantageous refinement of the invention provides that the carrier has a ring, which encloses the lancets. In this manner, the lancets may be protected from unintended contact during the handling of the lancet wheel. In addition, a lancet wheel can be grasped well on such a ring. The ring can be implemented without additional effort during the extrusion coating of the lancet wheel blank using plastic.

The carrier preferably forms a stop on one side of the lancet wheel, which only permits raising of the lancets in one direction. The stop can be implemented as a ring disk, for example. As a buckling guard, such a stop reduces the danger of damage of the lancet wheel or injury during the handling by unintentional bending of a web, because the lancets may be raised in only one direction due to the stop, namely away from the stop. In their starting position before the raising into the usage position, the lancets may rest on the stop or be positioned at a distance therefrom.

A further advantageous refinement of the invention provides that the lancet wheel has a hole in its center, using which it can be plugged onto a shaft of a lancing device, for example.

A further advantageous refinement of the invention provides that the lancet tips are enclosed by a sterile protector. The sterile protector can be injection molded around the lancet tips, for example, e.g. as foam. A sterile protector of this type is stripped off from the lancet tip on its own during a lancet puncture. A sterile protector may also be formed by film, for example, in that the lancet wheel blank is covered using film on both sides at least in the area of the lancet tips. By subsequent coating of the lancet wheel blank by injection molding of plastic, the sterile protective film may be fastened without additional effort. Upon raising of a lancet, the sterile protective film is pierced through in the area of the relevant lancet.

A further advantageous refinement of the invention provides that the lancet wheel has a handle, which extends perpendicularly to a wheel plane in which the lancets lie. Such a handle makes it easier to put the lancet wheel into a lancing device. The handle can be connected via an intended breakpoint to the lancet wheel. It is also possible to implement the handle separately and to connect it as needed to the actual lancet wheel, for example, in that the handle is plugged into a central hole.

A lancet wheel blank, which is cut out of metal to produce a lancet wheel according to the invention, having multiple annularly positioned lancets, which are radially aligned and have a lancet body ending in a lancet tip, and a carrier, to which the lancets are connected via radially running webs, which allow raising of the lancets into a usage position, can in principle also be used as a lancet wheel without injection molded plastic coating. Intended bending points may be predefined on the webs in such a case, for example, by punching through or another weakening of the web.

The lancet tips are preferably directed radially outward in a lancet wheel according to the invention. In this manner, the webs may originate radially from a common center, which allows advantageous simple manufacturing.

In a lancet wheel according to the invention, the plastic body, as the carrier body of the lancets, can advantageously form a lancet magazine, which allows simple handling and provides a coupling element for coupling on an advance unit of a lancing device. Therefore, by overmolding of a metal lancet wheel blank with plastic, a carrier body is preferably produced, which implements a coupling element for coupling on an advance unit of a lancing device, using which the lancets of the lancet wheel may be moved one after another into their usage position. In the simplest case, the coupling element can be an opening, for example, into which a shaft of an advance unit can be plugged. A lancet magazine formed by the plastic body can advantageously additionally cause protection of the lancets, for example, in that the carrier body has a ring which encloses the lancets.

BRIEF DESCRIPTION OF THE DRAWINGS

Further details and advantages of the invention are explained on the basis of exemplary embodiments with reference to the appended drawings. Identical parts and parts corresponding to one another are identified by corresponding reference numerals. In the figures.

DESCRIPTION OF SELECTED EMBODIMENTS

Figure 1:
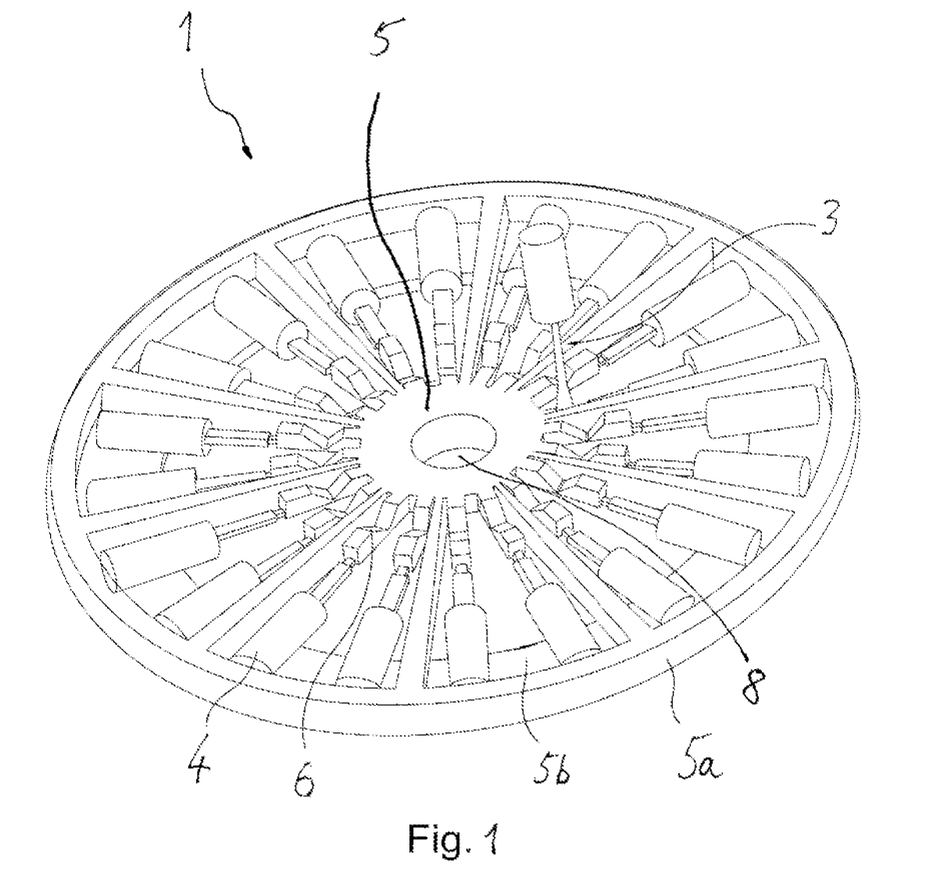
FIG. 1: shows an exemplary embodiment of a lancet wheel according to the invention.
Figure 2:
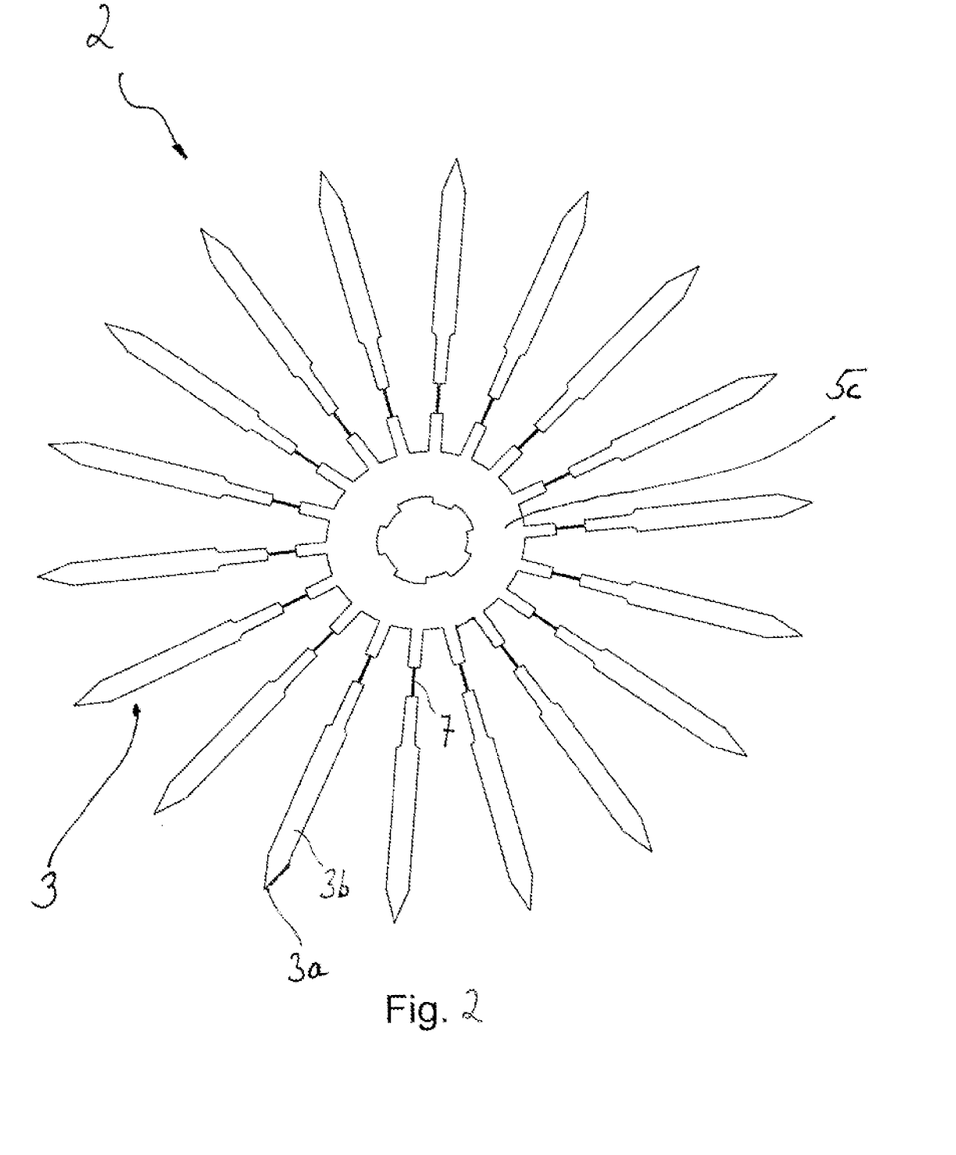
FIG. 2: shows the metal parts of the lancet wheel shown in FIG. 1.

FIG. 1 shows a lancet wheel 1, which was produced by insert molding the lancet wheel blank 2 shown in FIG. 2 with plastic. The lancet wheel 1 and/or the lancet wheel blank 2 comprise multiple annularly positioned lancets 3, which have a lancet body 3b made of metal ending in a lancet tip 3a. The lancet tips 3a are enclosed by a sterile protector 4, which is made of foam, for example, in the lancet wheel shown in FIG. 1, and are therefore not visible.

The lancet wheel 1 comprises a carrier 5, implemented as a frame, which carries the lancets 3. The lancets 3 are connected to the carrier 5 via webs 6, which allow raising of the lancets 3 into a usage position. The lancets 3 perform a pivot movement during the raising. A lancet 3 is shown in its raised usage position as an example in FIG. 1.

The webs 6 have a plastic body, which has an intended bending point, around which the webs are bent to raise the lancets. In the illustrated embodiment, the intended bending point is predefined by a notch in the plastic body. The plastic bodies of the webs 6 merge into the plastic body of the carrier 5. The plastic bodies of the webs 6 and the plastic body of the carrier 5 are produced as a one-piece injection-molded part during the coating of the lancet blank 2.

Metal webs 7, which originate from the lancet bodies 3b, of the lancet wheel blank 2 shown in FIG. 2 are embedded in the plastic bodies of the webs 6. The plastic body is wider than the metal webs 7 at the intended bending point, preferably at least twice as wide, in particular at least three times as wide, in the illustrated embodiment more than five times as wide. In this manner, the force required for raising the lancets 3 and thus for buckling the webs 6 is only insignificantly increased by the metal web 7.

The lancet tips 3a, which are directed radially outward, are enclosed by a ring 5a of the carrier 5 and protected in this manner from unintentional contact during the handling of the lancet wheel 1. The carrier 5 additionally has a stop 5b in the form of a ring disk, which permits raising of the lancets 3 in only one direction, namely away from the ring disk 5b. In this manner, the danger of damage to the lancet wheel 2 or an injury during the handling by unintentional bending of a web 6 is reduced.

In the illustrated exemplary embodiment, a further part of the carrier 5 is formed by a metal disk 5c of the lancet wheel blank 2, from which the metal web 7 originates. The metal disk 5c, a ring disk in the illustrated exemplary embodiment, is embedded in the plastic body of the carrier 5 by insert molding.

The plastic carrier body 5 of the lancet wheel 1 implements a lancet magazine in the illustrated exemplary embodiment, which makes it easier to handle the lancets and provides a coupling element for coupling to an advance unit of a lancing device, using which the lancets 3 of the lancet wheel 1 may be moved one after another into their usage position. The coupling element can be provided as a hole 8 for plugging onto a shaft of a lancing device, for example. The hole 8 can be positioned as a pocket hole or as a through hole in the carrier 5.

Figure 3:
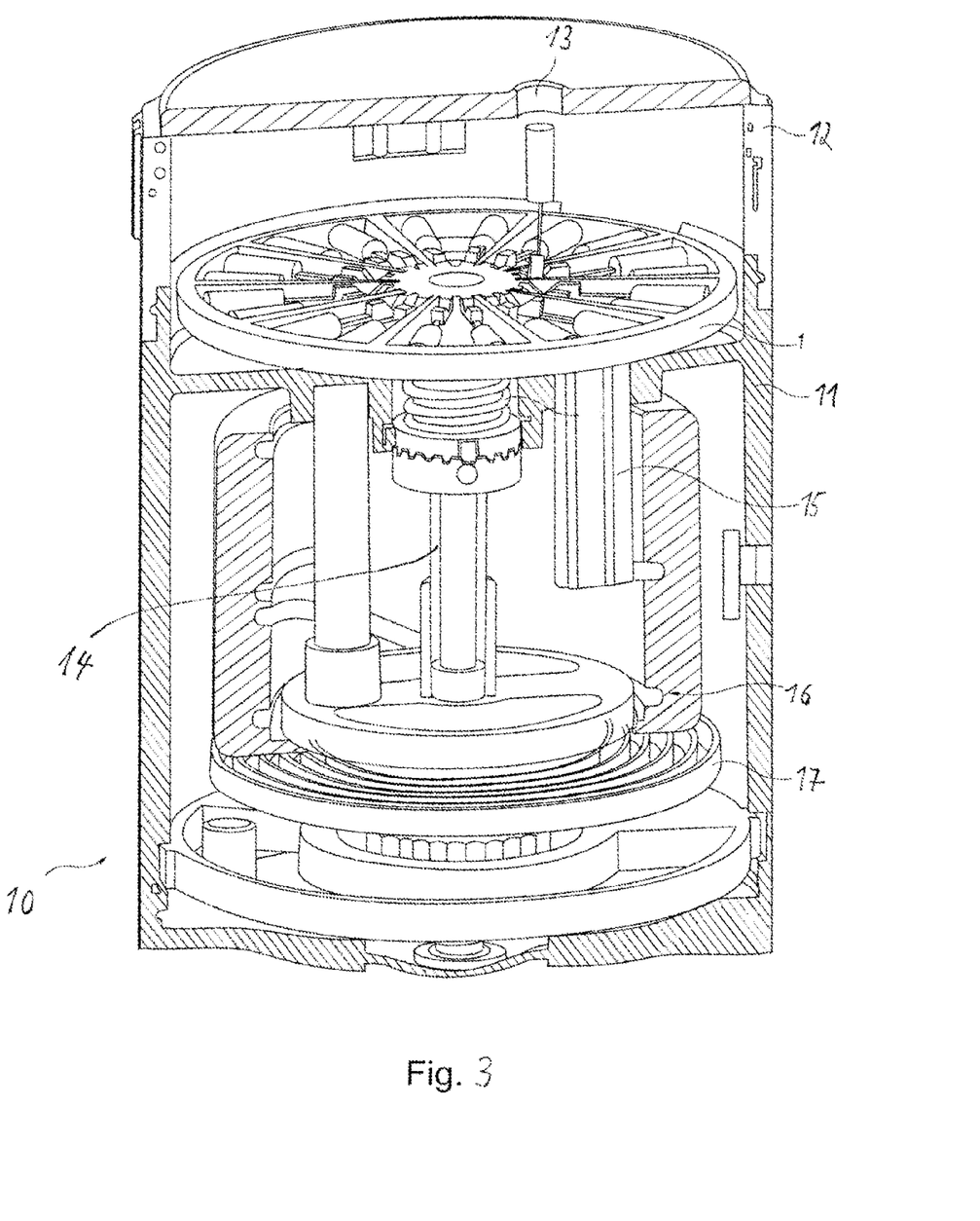
FIG. 3: shows an exemplary embodiment of a lancing system having the illustrated lancet wheel.

FIG. 3 shows an embodiment of a lancing device 10, which forms a lancing system together with a lancet wheel 1. The lancing device 10 comprises a housing 11 having a housing cap 12, which is removable for replacement of a lancet wheel 1. A housing opening 13, against which a body part can be pressed to produce a puncture wound, is positioned in the housing cap 12.

The lancet wheel 1 is plugged on a shaft 14 in the lancing device 10, using which the lancets 3 may be positioned for usage one after another by rotating the lancet wheel 1. The lancets 3 are raised into the usage position using a pivot unit 15, which is implemented in the illustrated embodiment as a slide movable in the puncture direction. If the slide 15 is displaced in the puncture direction, it encounters a lancet 3 positioned under the opening 13, so that it is raised into the usage position, in which its lancet tip 3a points toward the housing opening 13. Upon raising of the lancet 3, the webs 6 buckles at the intended bending point defined by the notch.

During a puncture, the lancing drive 16 of the illustrated lancing device 10 moves the entire lancet wheel 1 in the puncture direction. The force for this purpose is supplied by a drive spring 17, such as a coiled spring, which acts on a link controller via a rotor. The drive spring is tensioned using a tensioning disk, in that it is rotated by 180°. The lancet wheel is automatically incremented by one lancet 3 via a gearing, i.e., by 18° in the illustrated exemplary embodiment, because the lancet wheel 1 has twenty lancets 3.

The sterile protector 4 can remain on the lancet 3 during a puncture movement or can be removed beforehand. By providing the sterile protector 4 as foam, it is compressed when the lancet 3 hits a body part pressed against the housing opening 13 and therefore only insignificantly hinders the lancet movement.

As soon as a lancet 3 is no longer held by the slide 15 in its raised position, it snaps back into a flat location.

Figure 4:
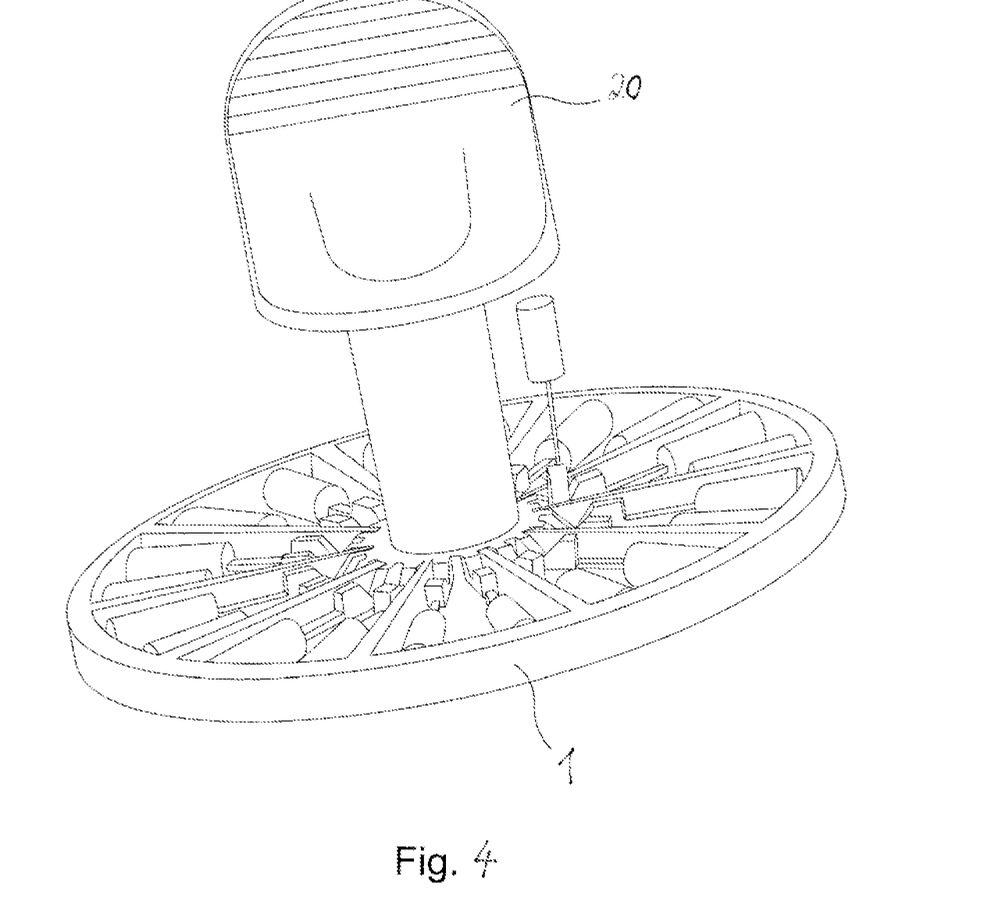
FIG. 4: shows the lancet wheel shown in FIG. 1 having a handle for insertion into a lancing device.

In order to make the insertion of the lancet wheel 1 into the lancing device 10 easier, the lancet wheel 1 can be provided with a removable handle 20, as shown in FIG. 11. A used lancet wheel 1 can be ejected from the lancing device 10 using an ejector by button pressing after the removal of the housing cap 12.

REFERENCE NUMERALS 1 lancet wheel
2 lancet wheel blank
3 lancets
3a lancet tip
3b lancet body
4 sterile protector
5 carrier
5a ring
5b stop
5c metal disk
6 web
7 metal web
8 hole
10 lancing device
11 housing
12 housing cap
13 housing opening
14 shaft
15 pivot unit
16 lancing drive
17 drive spring
20 handle

The invention claimed is:

1. A lancet wheel comprising:
    multiple annularly positioned lancets, which have a lancet body that is made of metal and ends in a lancet tip;
    a carrier, to which the lancets are connected via radially running webs, which allow raising of the lancets into a usage position;
    characterized in that the lancets are radially aligned and the webs have a plastic body, which predefines an intended bending point, around which the webs are bent to raise the lancets;
    wherein the lancet tip extends transverse to the lancet wheel when the lancet is bent at the bending point to the usage position, and
    wherein the lancet tip extends radially away from the carrier within a plane of the carrier prior to being bent to the usage position.

2. The lancet wheel according to claim 1, characterized in that the intended bending point is implemented as a notch in the plastic body.

3. The lancet wheel according to claim 1, characterized in that a metal web originating from the lancet body is embedded in the plastic body.

4. The lancet wheel according to claim 3, characterized in that the metal web extends through the intended bending point.

5. The lancet wheel according to claim 4, characterized in that the plastic body is wider at the intended bending point on the metal web.

6. The lancet wheel according to claim 3, characterized in that the carrier has a metal disk, to which the metal webs originating from the lancets lead.

7. The lancet wheel according to claim 1, characterized in that the carrier has a plastic body, which merges into the plastic bodies of the webs.

8. The lancet wheel according to claim 1, characterized in that the carrier has a ring, which encloses the lancets.

9. The lancet wheel according to claim 1, characterized in that the webs are elastically bendable around the intended bending point, so that a raised lancet passes into a flat location from the usage position without external force action.

10. The lancet wheel according to claim 1, characterized in that the carrier has a stop on one side of the lancet wheel, which only permits raising of the lancets in one direction.

11. The lancet wheel according to claim 5, wherein the plastic body is at least twice as wide at the intended bending point on the metal web.

12. The lancet wheel according to claim 5, wherein the plastic body is at least three times as wide at the intended bending point on the metal web.

13. A new lancet wheel comprising:
multiple annularly positioned lancets, which have a lancet body that is made of metal and ends in a lancet tip;
a carrier, to which the lancets are connected via radially running webs, which allow raising of the lancets from a starting position into a usage position;
wherein the lancets are radially aligned and the webs have a plastic body, which predifines an intended bending point, around which the webs are bent to raise the lancets;
wherein the lancet tip extends radially within a plane of the carrier when at the starting position; and
wherein the lancet tip extends out of the plane of the carrier when at the usage position.

14. A lancet wheel, comprising:
a carrier defining a plane;
a plurality of lancets having a lancet body that ends at a lancet tip, the lancet body being made of metal;
a plurality of webs connecting the lancets to the carrier, the webs running in a radial direction relative to the carrier, the webs being aligned in the radial direction with the lancets, the webs having a plastic body made plastic, the plastic body having a bending point;
wherein the webs are configured to bend at the bending point to move the lancet tip between a flat configuration and a usage position;
wherein the lancet tip at the flat configuration extends in the radial direction within the plane of the carrier; and
wherein the lancet tip at the usage position is raised out of the plane of the carrier.

15. The lancet wheel of claim 14, wherein the bending point is bent at right angles to usage point.

16. The lancet wheel of claim 14, wherein the bending point includes a notch defined in the plastic body.

* * * * *

UNITED STATES PATENT AND TRADEMARK OFFICE
CERTIFICATE OF CORRECTION

| | |
|---|---|
| PATENT NO. | : 9,066,689 B2 |
| APPLICATION NO. | : 12/891844 |
| DATED | : June 30, 2015 |
| INVENTOR(S) | : Michael Keil |

It is certified that error appears in the above-identified patent and that said Letters Patent is hereby corrected as shown below:

In the Claims

Col. 7, line 4, replace "A new lancet wheel comprising:" with --A lancet wheel comprising:--

Col. 7, line 11, replace "predifines" with --predefines--

Col. 8, line 16, replace "to usage point" with --the usage position--

Signed and Sealed this
Seventeenth Day of November, 2015

Michelle K. Lee
*Director of the United States Patent and Trademark Office*